United States Patent
Pheiffer et al.

(10) Patent No.: US 10,699,410 B2
(45) Date of Patent: Jun. 30, 2020

(54) AUTOMATIC CHANGE DETECTION IN MEDICAL IMAGES

(71) Applicant: Siemens Healthcare GmbH, Erlangen (DE)

(72) Inventors: Thomas Pheiffer, Philadelphia, PA (US); Shun Miao, Princeton, NJ (US); Rui Liao, Princeton Junction, NJ (US); Pavlo Dyban, Berlin (DE); Michael Suehling, Erlangen (DE); Tommaso Mansi, Plainsboro, NJ (US)

(73) Assignee: Siemes Healthcare GmbH, Erlangen (DE)

( * ) Notice: Subject to any disclaimer, the term of this patent is extended or adjusted under 35 U.S.C. 154(b) by 125 days.

(21) Appl. No.: 16/028,787

(22) Filed: Jul. 6, 2018

(65) Prior Publication Data
US 2019/0057505 A1    Feb. 21, 2019

Related U.S. Application Data

(60) Provisional application No. 62/546,758, filed on Aug. 17, 2017.

(51) Int. Cl.
*G06K 9/00*   (2006.01)
*G06T 7/00*   (2017.01)
(Continued)

(52) U.S. Cl.
CPC ............ G06T 7/0016 (2013.01); G06T 7/136 (2017.01); A61B 5/0033 (2013.01); A61B 5/055 (2013.01);
(Continued)

(58) Field of Classification Search
CPC ... G06T 7/0016; G06T 7/136; G06T 2200/04; G06T 2207/10081; G06T 2207/20021; A61B 5/0033; A61B 5/055
(Continued)

(56) References Cited

U.S. PATENT DOCUMENTS 6,463,438 B1 * 10/2002 Veltri .................. G06K 9/0014
                                                                706/15
6,690,371 B1 *  2/2004 Okerlund .............. G06T 11/008
                                                                345/424
(Continued)

OTHER PUBLICATIONS

Ko, Jane P., and Margrit Betke. "Chest CT: automated nodule detection and assessment of change over time—preliminary experience." Radiology 218.1 (2001): 267-273.
(Continued)

*Primary Examiner* — Marceau Milord

(57) ABSTRACT

Systems and methods are provided for identifying pathological changes in follow up medical images. Reference image data is acquired. Follow up image data is acquired. A deformation field is generated for the reference image data and the follow up data using a machine-learned network trained to generate deformation fields describing healthy, anatomical deformation between input reference image data and input follow up image data. The reference image data and the follow up image data are aligned using the deformation field. The co-aligned reference image data and follow up image data are analyzed for changes due to pathological phenomena.

20 Claims, 7 Drawing Sheets

(51) Int. Cl.
*G06T 7/136* (2017.01)
*A61B 5/00* (2006.01)
*A61B 5/055* (2006.01)

(52) U.S. Cl.
CPC .... *G06T 2200/04* (2013.01); *G06T 2207/10081* (2013.01); *G06T 2207/20021* (2013.01); *G06T 2207/20076* (2013.01); *G06T 2207/20081* (2013.01); *G06T 2207/20084* (2013.01); *G06T 2207/20224* (2013.01); *G06T 2207/30004* (2013.01); *G06T 2207/30061* (2013.01)

(58) Field of Classification Search
USPC .......................................... 382/128, 131, 103
See application file for complete search history.

(56) References Cited

U.S. PATENT DOCUMENTS

| | | | |
|---|---|---|---|
| 9,760,690 B1* | 9/2017 | Petkov | G06T 15/08 |
| 9,773,311 B2* | 9/2017 | Ross | G06T 7/136 |
| 10,049,301 B2* | 8/2018 | Kluckner | G06K 9/6265 |
| 10,096,107 B2* | 10/2018 | Ghesu | G06T 7/0012 |
| 10,169,871 B2* | 1/2019 | Hibbard | G06T 7/38 |
| 10,339,695 B2* | 7/2019 | Petkov | G06F 19/321 |
| 10,475,165 B2* | 11/2019 | Vogels | G06K 9/40 |
| 2005/0197981 A1 | 9/2005 | Bingham | |
| 2007/0003117 A1 | 1/2007 | Wheeler et al. | |
| 2007/0225553 A1* | 9/2007 | Shahidi | A61B 5/064 600/103 |
| 2008/0144773 A1* | 6/2008 | Bar-Zohar | A61B 1/00096 378/98.12 |
| 2011/0251454 A1* | 10/2011 | Robb | A61B 1/31 600/103 |
| 2012/0069167 A1* | 3/2012 | Liu | A61B 6/584 348/65 |
| 2013/0004044 A1* | 1/2013 | Ross | G06T 7/136 382/131 |
| 2013/0208241 A1* | 8/2013 | Lawson | A61B 3/0091 351/206 |
| 2016/0321523 A1* | 11/2016 | Sen | G06T 5/002 |
| 2017/0016920 A1* | 1/2017 | Coimbra | G01N 33/56911 |
| 2017/0161607 A1* | 6/2017 | English | G06F 3/017 |
| 2017/0185740 A1* | 6/2017 | Seegerer | A61B 6/032 |
| 2017/0255745 A1* | 9/2017 | Mihalef | G06F 17/11 |
| 2017/0337682 A1* | 11/2017 | Liao | G06T 7/30 |
| 2018/0218502 A1* | 8/2018 | Golden | G06N 3/08 |
| 2019/0108635 A1* | 4/2019 | Hibbard | G06T 7/38 |
| 2019/0370970 A1* | 12/2019 | Kim | G06T 7/0016 |

OTHER PUBLICATIONS

Myronenko, Andriy, and Xubo Song. "Point set registration: Coherent point drift." IEEE transactions on pattern analysis and machine intelligence 32.12 (2010): 2262-2275.
Sakamoto, Ryo, et al. "Detection of time-varying structures by large deformation diffeomorphic metric mapping to aid reading of high-resolution CT images of the lung." PloS one 9.1 (2014): e85580.
Viergever, Max A., et al. "A survey of medical image registration—under review." Medical image analysis 33 (2016): 140-144.
European Search Report dated Nov. 29, 2018 in corresponding European Patent Application No. 18189306.6.
Havaei Mohammad et al: "Deep Learning Trends for Focal Brain Pathology Segmentation in MRI"; Dec. 10, 2016 (Dec. 10, 2016), International Conference on Simulation, Modeling, and Programming for Autonomous Robots,SIMPAR 2010; [Lecture Notes in Computer Science; Lect.Notes Computer], Springer, Berlin, Heidelberg; pp. 125-148.
Ghesu Florin C et al: "Marginal Space Deep Learning: Efficient Architecture for Volumetrie Image Parsing"; IEEE Transactions on Medical Imaging, IEEE Service Center, Piscataway, NJ, US, vol. 35, No. 5, May 1, 2016 (May 1, 2016); ppl 1217-1228.

* cited by examiner

AUTOMATIC CHANGE DETECTION IN MEDICAL IMAGES

CROSS REFERENCE TO RELATED APPLICATIONS

This application claims the benefit of U.S. Provisional Application No. 62/546,758, filed Aug. 17, 2017, which is hereby incorporated by reference in its entirety.

FIELD

The present embodiments relate to medical image processing, such as image processing for computed tomography images or magnetic resonance images.

BACKGROUND

Image quality for follow up reading and longitudinal change assessment is an important task in medical imaging techniques such as computed tomography (CT) or magnetic resonance imaging (MRI). The task of recognizing changes in medical images is a technical problem due to the challenge of distinguishing pathological from normal changes in the medical images. For example, for a follow up scan of a lung or other organ of a patient, normal changes such as respiration or normal anatomical differences may mask pathological changes such as cancerous nodule growth or shrinkage.

Detecting pathological changes in CT images or MRI images acquired at two or more time points is difficult due to the large amount of normal changes that may occur. Manual detection of normal vs pathological changes may be difficult or error prone. Computer-assisted image registration may be used to provide an improvement and increase in objectivity of the results. Image registration may be categorized into two groups: rigid and non-rigid. Non-rigid image registration is also known as deformable image registration (DIR). In rigid image registration (RIR), all pixels move and/or rotate uniformly so that every pixel-to-pixel relationship remains the same before and after transformation. In DIR, however, the pixel-to-pixel relationships change, to model a non-linear deformation.

RIR is very effective in cases when no anatomic change nor deformations are expected. However, some patients may experience anatomical structure changes due to weight loss, tumor shrinkage, and/or physiological organ shape variation. The changes may not be handled well by RIR. In comparison to RIR, DIR has a significantly greater flexibility. DIR can manage local distortion between two image sets (e.g. anatomical structure changes). For DIR, mathematical modeling uses known information to find a statistic of motion or deformation in considered organs. Segmentation uses the information to map a contour from a reference image to updated images. DIR may detect and use anatomical landmarks to register sets of images. The methods, however do not distinguish between normal anatomical changes and pathological changes. In an example, a growth of a tumor may be suppressed in a follow up image if the DIR is too strong. Current computer-assisted tools such as DIR may be inaccurate due to normal anatomical changes represented in the images and an inability to distinguish abnormal changes are normal changes and as such, provide inconsistent and confusing image registration.

SUMMARY

By way of introduction, the preferred embodiments described below include embodiments for detecting pathological changes in medical images acquired at two or more time points. A machine-learned network assists in aligning reference and follow up images following a biomechanical prior. The aligned reference and follow up images are analyzed to identify the pathological changes which then may be presented to an operator.

In a first aspect, a method is provided for identifying pathological changes in follow up medical images. Reference image data is acquired at a first time. Follow up image data is acquired at a subsequent time. A deformation field is generated for the reference image data and the follow up data using a machine-learned network trained to generate deformation fields describing healthy, anatomical deformation between input reference image data and input follow up image data. The reference image data and the follow up image data are aligned using the deformation field. The co-aligned reference image data and follow up image data are analyzed for changes due to pathological phenomena.

In a second aspect, a method is provided for training a neural network to generate a physiological deformation field between a reference volume and a follow up volume. A plurality of paired reference volumes and follow up volumes are acquired. The plurality of pairs of volumes are segmented. The segmented pairs are converted to a plurality of mesh surfaces. The mesh surfaces of the plurality of pairs of volumes are matched using point-wise correspondences. Biomechanical motion is solved for the matched mesh surfaces using a finite element method. A deformation mesh is generated for a paired set of volumes using the mesh surfaces and the motion. The paired set of volumes are input into the neural network configured to output a physiological deformation field. The deformation mesh and the physiological deformation field are compared. Weights are adjusted in the neural network as a function of the comparison. Generating, inputting, comparing, and adjusting are repeated with paired sets of volumes until the neural network outputs a physiological deformation field that is similar to the deformation field.

In a third aspect, a system is provided for identifying pathological changes in follow up medical images for a patient. The system includes a machine learned network and an image processor. The machine-learned network is configured to generate a physiological deformation field between a reference image and a follow up image. The image processor is configured to warp the follow up image as a function of the physiological deformation field; the image processor further configured to identify a difference from the warped follow up image from the reference image; the image processor further configured to highlight the difference between the warped follow up image and the reference image as the pathological changes.

The present invention is defined by the following claims, and nothing in this section should be taken as a limitation on those claims. Further aspects and advantages of the invention are discussed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION

Pathological differences are automatically detected and highlighted in medical images like computed tomography (CT), magnetic resonance images (MRI) or other modalities. A machine-learned neural network automatically aligns follow up medical imaging data to medical imaging reference data in a way that removes or reduces normal anatomical and physiological differences, such that the remaining differences due to pathology may be highlighted.

A biomechanical model is generated that identifies the normal anatomical and physiological differences. The neural network is trained using the biomechanical model to produce deformation fields given input volume data. The deformation fields are used to align the reference volume data with the follow up volume data. The alignment is used to identify pathological differences between the two data sets. The pathological differences may be highlighted in an image or otherwise presented to an operator.

In an example, the approach may significantly decrease the time spent by doctors on reading lung scans of a patient, for example, by improving the rate of early detection of tumor change. The approach may be applied to patients participating in lung screening programs to compare reference and follow up images. Example applications for lung scans include for highlighting cancerous nodule growth or shrinkage, or detection of diffuse changes in lungs with chronic obstructive pulmonary disease (COPD). The approach may be applied in various imaging situations, such as for different imaging modalities (e.g., CT, MRI, or ultrasound) and/or for other anatomy (e.g., liver, prostate, breast) to for example, detect cancerous growths or shrinkage or other medical diagnoses.

Figure 1:
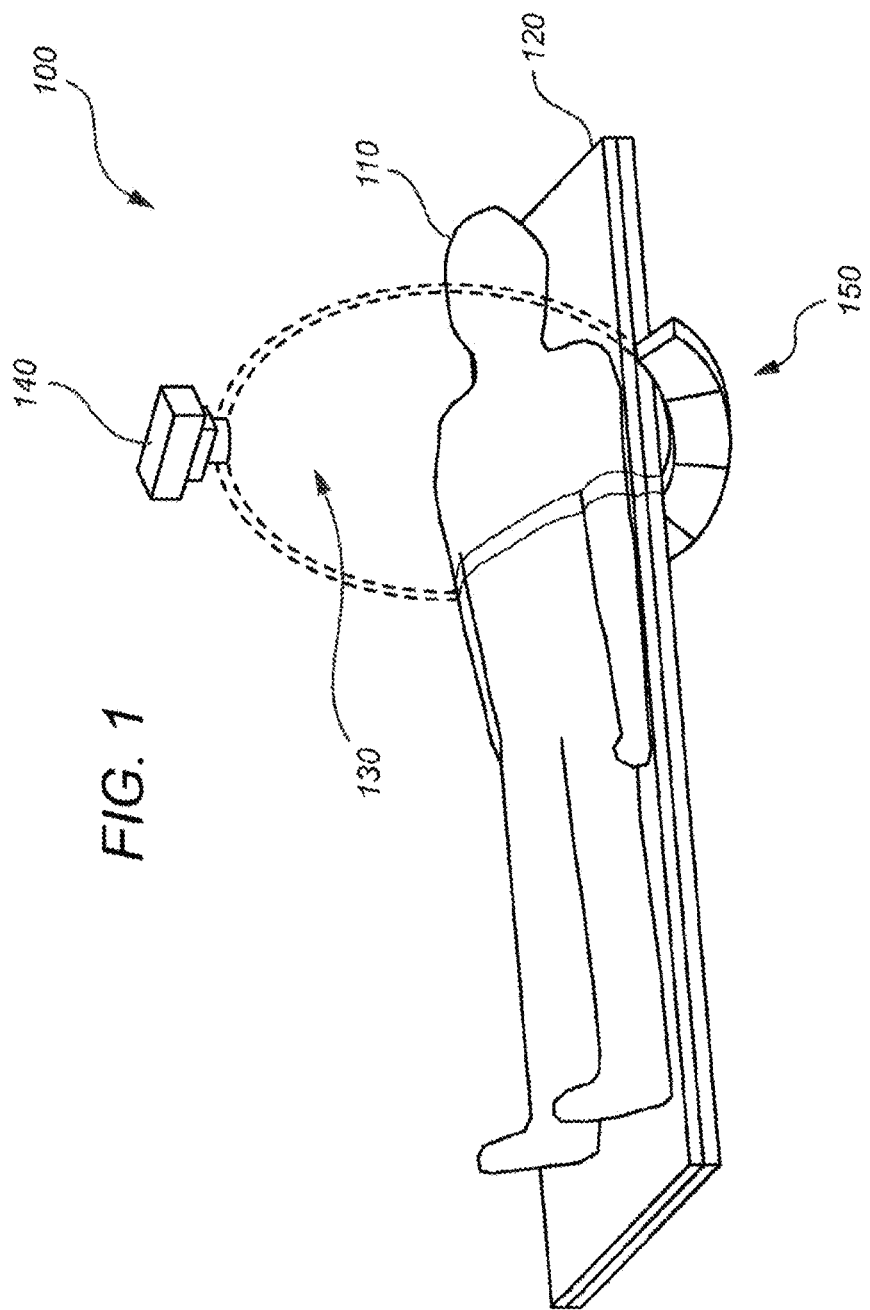
FIG. 1 depicts an example of a medical imaging system.

FIG. 1 depicts an example CT imaging system 100. An object 110 (e.g., a patient) may be positioned on a table 120 that is configured, via a motorized system, to move the table to multiple positions through a circular opening 130 in the CT imaging system 100. An X-ray source 140 (or other radiation source) and detector element(s) 150 are a part of the CT imaging system and are configured to rotate around the subject 110 while the subject is inside the opening 130. The rotation may be combined with movement of the bed to scan along a longitudinal extent of the patient. Alternatively, the gantry moves the source 140 and detector 150 in a helical path about the patient. In a CT imaging system 100, a single rotation may take approximately one second or less. During the rotation of the X-ray source 140 and/or detector, the X-ray source 140 produces a narrow, fan-shaped (or cone-shaped) beam of X-rays that pass through a targeted section of the body of the subject 110 being imaged. The detector element(s) 150 (e.g., multi-ring detector elements) are opposite the X-ray source 140 and register the X-rays that pass through the body of the subject being imaged and, in that process, record a snapshot used to create an image. Many different snapshots at many angles through the subject are collected through one rotation of the X-ray source 140 and/or detector element(s) 150. The image data generated by the collected snapshots are transmitted to a control unit that stores or processes the image data based on the snapshots into one or several cross-sectional images or volumes of an interior of the body (e.g., internal organs or tissues) of the subject being scanned by the CT imaging system 100.

When capturing CT data at different times (e.g., different imaging appointments occurring hours, days, weeks, months, or years apart), one problem that arises, is comparing the different sets of data against one another. Objects, e.g. patients, change over time, growing and shrinking, losing mass, gaining mass, changing shape, etc. Further, for example, when scanning the lungs, respiratory motion or other motion may confound image alignment. Aligning images rigidly allows some changes in images to be easily detected. However, such an alignment does not model changes from e.g. organ deformation, patient weight loss, anatomical movement, or shrinkage. Accurate assessment of imaging information may require DIR to resolve anatomical movement. DIR is a method for finding the mapping between points in one image and the corresponding point in another image. Because of anatomical variations occurring during the treatment or over time and differences in the breathing state from one image to another, DIR has been considered an important tool to provide accurate longitudinal mapping of soft tissues (e.g. lung).

Figure 2B:
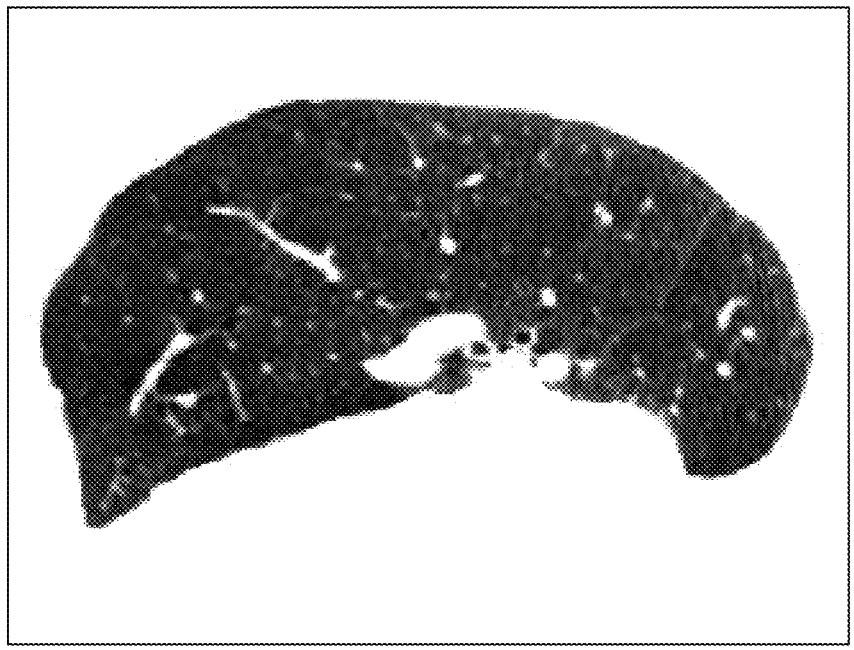
FIGS. 2A and 2B depicts example computed tomography images.
Figure 2A:
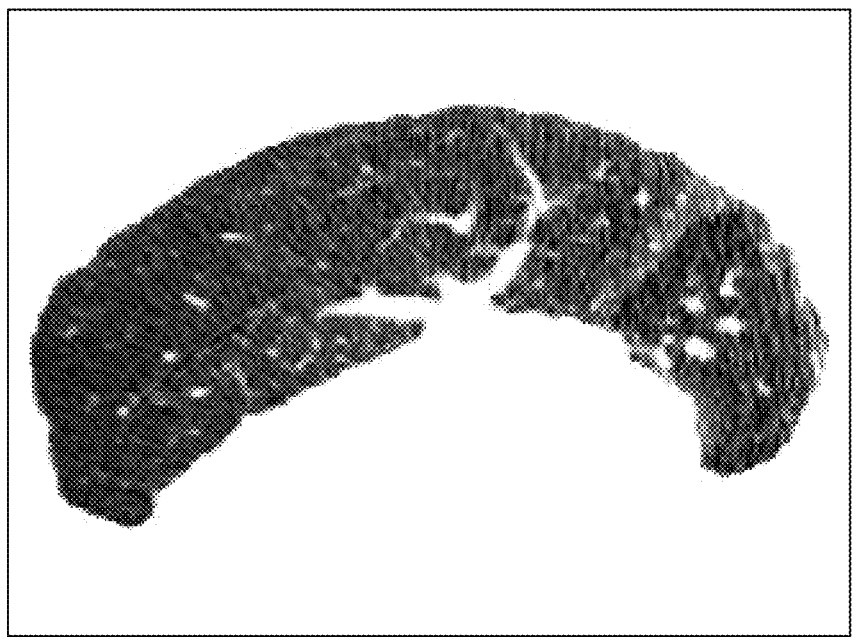

FIGS. 2A and 2B depict two lungs images from a patient acquired at two different time points. FIG. 2A depicts an initial reference CT image. FIG. 2B depicts a follow up CT image. As depicted, there are both pathological and normal changes in the follow up CT image as compared to the reference CT image. For example, certain tissues may have expanded, or certain boundaries may have moved. RIR may not be able to register the two images due to deformation in the scan area. DIR may register the two images but may also alter the pathological change which may lead to an incorrect diagnosis. For example, DIR may shrink a tumor as a DIR algorithm may not take into consideration pathological changes. An operator who views the resulting image may not comprehend the size of the tumor as a result of the erroneous registration.

An image-to-image network may be used to register while minimizing distortion to pathological changes due to anatomical changes. The disclosed image-to-image networks may be implemented to computationally facilitate processing of medical imaging data and consequently improving and optimizing medical diagnostics. Detection and highlighting pathological changes in medical images allows for an increased efficiency and usage of resources. Less time may be spent on a patient by a doctor or an operator for diagnosis of a medical condition. Improved visibility of pathological changes may lead to better diagnosis of medical ailments. Improved diagnosis may lead to improved medical outcomes. The image-to-image network provides a technical solution for registration to improve diagnostic quality of medical imaging of the patient.

Figure 3:
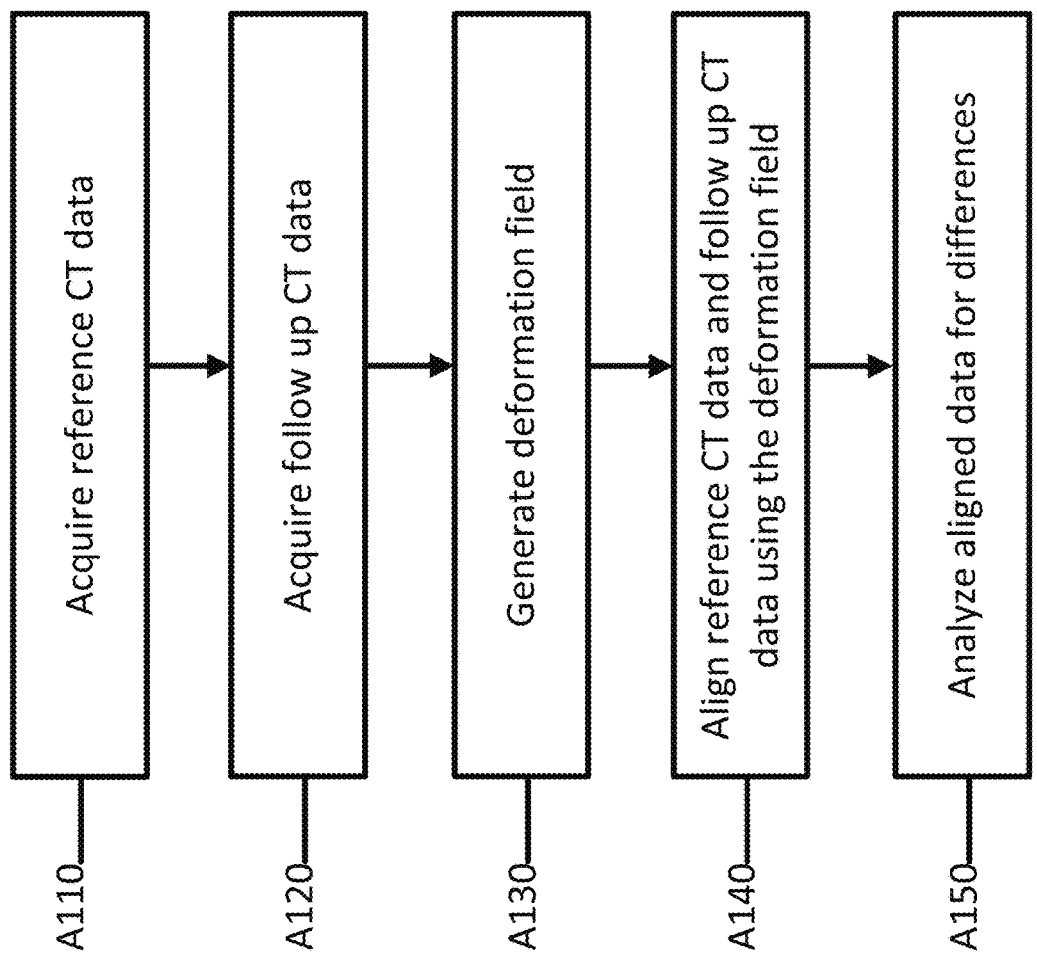
FIG. 3 depicts a method for detecting pathological changes in CT images acquired at two or more time points according to an embodiment.

FIG. 3 depicts an example method for detecting and highlighting pathological changes in follow up CT data. A machine-learned network is used to biomechanically align the CT data followed by highlighting of relevant pathological phenomena. The machine-learned network is an artificial neural network that is pre-trained on sets of image pairs (reference and follow up) that have already been aligned using a biomechanical tissue model to produce a deformation field for each image pair. Once trained, the machine-learned network produces a new deformation field for unseen image pairs where deformations for anatomical or motion differences are minimized while pathological differences are maintained. The deformation field is used to co-align the new pairs. The residual image differences after co-alignment are analyzed and used as input to further image processing to highlight pathological changes.

Figure 4:
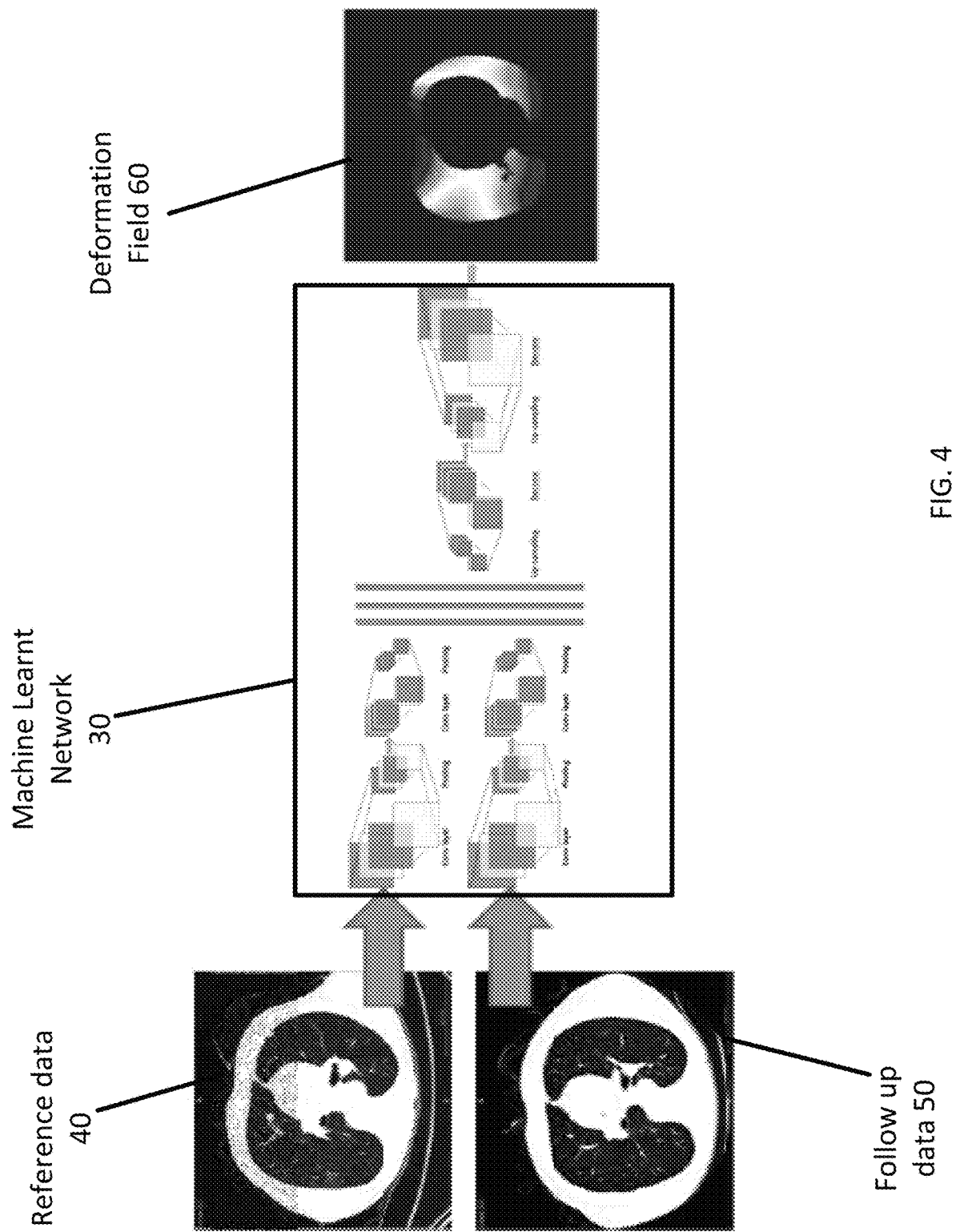
FIG. 4 depicts a machine-learned network trained to generate a deformation field according to an embodiment.
Figure 7:
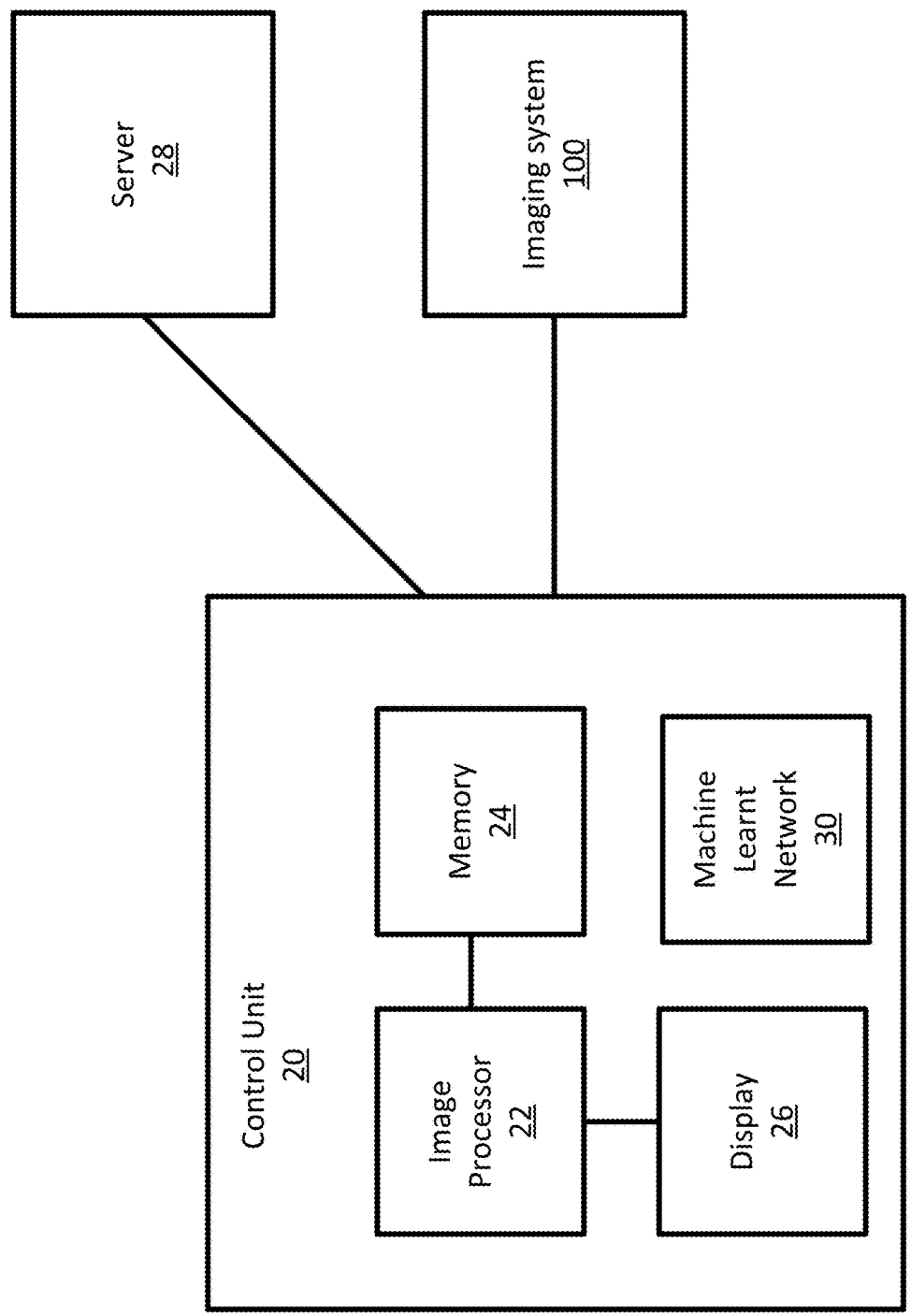
FIG. 7 depicts a system for detecting pathological changes in CT images acquired at two or more time points according to an embodiment.

The acts are performed by the system of FIG. 1, FIG. 4, FIG. 7, other systems, a workstation, a computer, and/or a server. Additional, different, or fewer acts may be provided. The acts are performed in the order shown (e.g., top to bottom) or other orders.

At act A110, reference CT data is acquired at a first time by a medical imaging device. The CT data may be acquired from a medical imaging device. The CT data may be processed into images or may be imaging data (e.g. medical imaging data) to be used to form an image. The data, images, or imaging data is made available by or within the medical imaging device. Alternatively, the acquisition is from storage or memory, such as acquiring a previously created dataset from a picture archiving and communication system (PACS). A processor may extract the data from a picture archive communications system or a medical records database.

The CT data is data representing a two-dimensional slice or a three-dimensional volume of the patient. For example, the CT data represents an area or slice of the patient as pixel values. As another example, the CT data represents a volume or three-dimensional distribution of voxels. The three-dimensional representation may be formatted as a stack or plurality of two-dimensional planes or slices. Values are provided for each of multiple locations distributed in two or three dimensions.

The data may be in any format. While the terms image and imaging are used, the image or imaging data may be in a format prior to actual display of the image. For example, the imaging data may be a plurality of scalar values representing different locations in a Cartesian or polar coordinate format different than a display format. As another example, the image may be a plurality red, green, blue (e.g., RGB) values output to a display for generating the image in the display format. The imaging data may be currently or previously displayed image in the display or another format. The imaging data is a dataset that may be used for imaging, such as scan data or a generated image representing the patient.

Any type of medical imaging data and corresponding medical scanner may be used. In one embodiment, the imaging data is a computed tomography (CT) image acquired with a CT system. For example, a chest CT dataset may be acquired by scanning the lungs. The output image may be a two-dimensional image slice. For a three-dimensional CT image, the raw data from the detector is reconstructed into a three-dimensional representation. As another example, magnetic resonance (MR) data representing a patient is acquired with an MR system. The data is acquired using an imaging sequence for scanning a patient. K-space data representing an interior region of a patient is acquired. Fourier analysis is performed to reconstruct the data from the k-space into a three-dimensional object or image space. The data may be ultrasound data. Beamformers and a transducer array scan a patient acoustically. Received acoustic signals are beamformed and detected into polar coordinate ultrasound data representing the patient.

The imaging data represents tissue, fluid, and/or bone of the patient. For imaging the lungs, the imaging data may include response from the lungs and the anatomy around the lungs (e.g., upper torso). In other embodiments, the medical image represents both function (such as perfusion) as well as structure, such as nuclear medicine (NM) data.

The medical imaging data is acquired as one or more frames of data. The frame of data represents the scan region at a given time or period. The dataset may represent the area or volume over time, such as providing a 4D representation of the patient. The medical imaging data may be captured over different phases for a patient. Breathing phases, for example, may be tracked and combined with the medical imaging data to identify phase timing for the medical imaging data. The data may be labeled with the phase at which the data was acquired. For example, the phase may include peak inhale, early inhale, mid inhale, end inhale, peak exhale, and/or early exhale among other respiratory phase time points.

At act A120, follow up CT data is acquired at a second time. Similar to act A110, the data, images, or imaging data is made available by or within the medical imaging device. Alternatively, the acquisition is from storage or memory, such as acquiring a previously created dataset from a picture archiving and communication system (PACS). A processor may extract the data from a picture archive communications system or a medical records database. The second time is a subsequent time later than the first time. The second time may be hours, days, week, months, or years after the first time. There may be intervening scans or procedures between the first time and the second time. In an embodiment, the follow up CT data is acquired using the same or similar settings and parameters as the reference CT data. Similar settings and parameters may include, for example, the same medical imaging device, a same dose, the same phase timing, x-ray source voltage, among others. The follow up CT data may be collected at different phases for a patient. The data may be labeled with the phase at which the data was acquired. For example, for lung data the phase may include peak inhale, early inhale, mid inhale, end inhale, peak exhale, and/or early exhale among other respiratory phase time points.

At act A130, a deformation field for the reference CT data and the follow up CT data is generated using a machine-learned network trained to generate deformation fields describing anatomical deformation between input reference CT data and input follow up CT data. In an embodiment, the machine-learned network is trained to generate a deformation field that is similar to a deformation field generated by a biomechanical model. The biomechanical model is generated from a cohort of reference and follow up CT data. The output of the biomechanical model is a deformation mesh that describes the anatomical movement or normal changes between pairs of reference and follow up data. The machine-learned network is trained on the cohort of reference and follow up CT data to generate a deformation field that is similar to one derived from the deformation mesh. To train the network, the generated deformation field is compared against the deformation field from the biomechanical model. The comparison (e.g. difference), namely the loss function, is used to provide feedback to the network so that weights of the network may be adjusted to generate a better output deformation field. The process may be repeated multiple times until the deformation field is similar to one derived from the deformation mesh.

The machine-learned network may be any type of neural network that is trained to generate a deformation field. In an embodiment, the machine-learned network is an image-to-image network.

FIG. 4 depicts an example representation of an image-to-image network trained to generate a deformation field. The machine-learned network 30 takes as input reference data 40 (here depicted as a 2D image) and follow up data 50 (here depicted as a 2D image). The machine-learned network 30 includes a plurality of layers and nodes that are weighted. The machine-learned network 30 outputs a deformation field 60 that is indicative of the deformation due to anatomical deformation between the reference data 40 and follow up data 50. The deformation field 60 is compared to a deformation field generated by a biomechanical model (that uses the reference and follow up data). The comparison is used to adjust the weights of the nodes in the machine-learned network 30. The process of inputting data, outputting a deformation field, and adjusting weights may be repeated until the output deformation field is similar to the deformation field generated by a biomechanical model. The trained machine-learned network 30 may then be used to generate deformation fields for unseen reference and follow up data pairs.

In one embodiment, the arrangement of the machine-learned network 30 is a neural network for deep learning. Other network arrangements may be used, such as a support vector machine. Deep architectures include convolutional neural network (CNN) or deep belief nets (DBN), but other deep networks may be used. CNN learns feed-forward mapping functions while DBN learns a generative model of data. In addition, CNN uses shared weights for all local regions while DBN is a fully connected network (e.g., including different weights for all regions of an image). The training of CNN is entirely discriminative through back-propagation. DBN, on the other hand, employs the layer-wise unsupervised training (e.g., pre-training) followed by the discriminative refinement with back-propagation if necessary. In an embodiment, the arrangement of the machine learnt network is a fully convolutional network (FCN). Alternative network arrangements may be used, for example, a 3D Very Deep Convolutional Networks (3D-VGGNet). VGGNet stacks many layer blocks containing narrow convolutional layers followed by max pooling layers. A 3D Deep Residual Networks (3D-ResNet) architecture may be used. A Resnet uses residual blocks and skip connections to learn residual mapping.

The machine-learned network 30 is defined as a plurality of sequential feature units or layers. Sequential is used to indicate the general flow of output feature values from one layer to input to a next layer. The information from the next layer is fed to a next layer, and so on until the final output. The layers may only feed forward or may be bi-directional, including some feedback to a previous layer. The nodes of each layer or unit may connect with all or only a sub-set of nodes of a previous and/or subsequent layer or unit. Skip connections may be used, such as a layer outputting to the sequentially next layer as well as other layers.

Rather than pre-programming the features and trying to relate the features to attributes, the deep architecture is defined to learn the features at different levels of abstraction based on an input image data with or without pre-processing. The features are learned to reconstruct lower level features (i.e., features at a more abstract or compressed level). For example, features for reconstructing an image are learned. For a next unit, features for reconstructing the features of the previous unit are learned, providing more abstraction. Each node of the unit represents a feature. Different units are provided for learning different features.

Various units or layers may be used, such as convolutional, pooling (e.g., max-pooling), deconvolutional, fully connected, or other types of layers. Within a unit or layer, any number of nodes is provided. For example, 100 nodes are provided. Later or subsequent units may have more, fewer, or the same number of nodes. In general, for convolution, subsequent units have more abstraction. For example, the first unit provides features from the image, such as one node or feature being a line found in the image. The next unit combines lines, so that one of the nodes is a corner. The next unit may combine features (e.g., the corner and length of lines) from a previous unit so that the node provides a shape indication. For transposed-convolution to reconstruct, the level of abstraction reverses. Each unit or layer reduces the level of abstraction or compression.

The features of the nodes are learned by the machine using any building blocks. For example, auto-encoder (AE) or restricted Boltzmann machine (RBM) approaches are used. AE transforms data linearly, and then applies a non-linear rectification, like a sigmoid function. The objective function of AE is the expected mean square error between the input image and reconstructed images using the learned features. AE may be trained using stochastic gradient descent or other approach to learn, by the machine, the features leading to the best reconstruction. The objective function of RBM is an energy function. Exact computation of the likelihood term associated with RBM is intractable. Therefore, an approximate algorithm, such as contrastive-divergence based on k-step Gibb sampling or other, is used to train the RBM to reconstruct the image from features.

The loss function used to train the machine-learned network 30 may be based on the difference between an output deformation field and a deformation field generated by the biomechanical model. The loss function may be, for example, a mean square error of the difference.

The machine-learned network 30 is trained as an image-to-image neural network to generate deformations fields from a reference image and a follow-up image that are similar to the deformation field of the biomechanical model. For training, the machine-learned network 30 takes two CT images (image data, image volumes) into its input layer, and the output layer is a generated deformation field image that is compared to a model-generated field. The deformation comparison is used as a loss function of the machine-learned network 30. The loss is used to iteratively adjust the internal weights of the machine-learned network 30 until the network is able to generate deformation fields that are similar to the modelled deformations across the large cohort of training data.

At act A140, the reference CT data and the follow up CT data are aligned with one another using the deformation field. The biomechanical model that the machine learned network is trained to mimic represents deformation due to anatomy and/or motion. Change due to alteration of pathology is not provided. As a result, the machine-learned network estimates the deformation field for anatomy and/or motion without including pathology-based deformation. Aligning the reference CT data and follow up CT data may include point to point registration and/or warping the data to match the deformation. The outputted aligned pair may include similar boundaries due to the alignment, but any pathological phenomena may not be affected.

At act A150, the aligned reference CT data and follow up CT data are compared to identify changes due to pathological phenomena. In an embodiment, the changes are highlighted for display to an operator. One method to highlight the pathological changes is to subtract the biomechanically-aligned images from one another. The difference may be highlighted. The highlighting may draw attention to areas in the follow up CT image where there are likely changes due to pathological phenomena such as nodule growth. The type of change is likely to be of a different mode than the biomechanical motion model (and machine-learned network 30). The difference image will have the largest magnitudes in areas of large change, such as the border around an expanding tumor or indications of tissue diseases like emphysema, etc.

Another method to highlight the change includes visualization of the magnitude of the deformation field. An intensity-based deformable registration algorithm may match the different outlines of an abnormal growth in the baseline and the follow up scans. The magnitude of the deformation may describe the scale of the change of the abnormality volume. The magnitude volume may be visualized as a heat map.

In an embodiment, a method for change highlighting uses a patch-based network that is trained to detect pathological changes in the follow up image. The training of the neural network makes use of the fact that lesion changes cause large anatomical deformation or mismatch in point correspondences that are still present after the images have been aligned. A fully convolutional, image-to-image neural network may be used in which corresponding patches in the reference and follow up image are input into the network, and the output is a likelihood heat map of change. The network may be trained using ground truth data that has been manually annotated. Any type of image-to-image neural network may be used. Alternative machine-learned networks may be used that are configured or trained to identify changes between the aligned reference and follow up images. The heat map may be visualized as an overlay image on the follow up CT to help guide the image reading.

Figure 5:
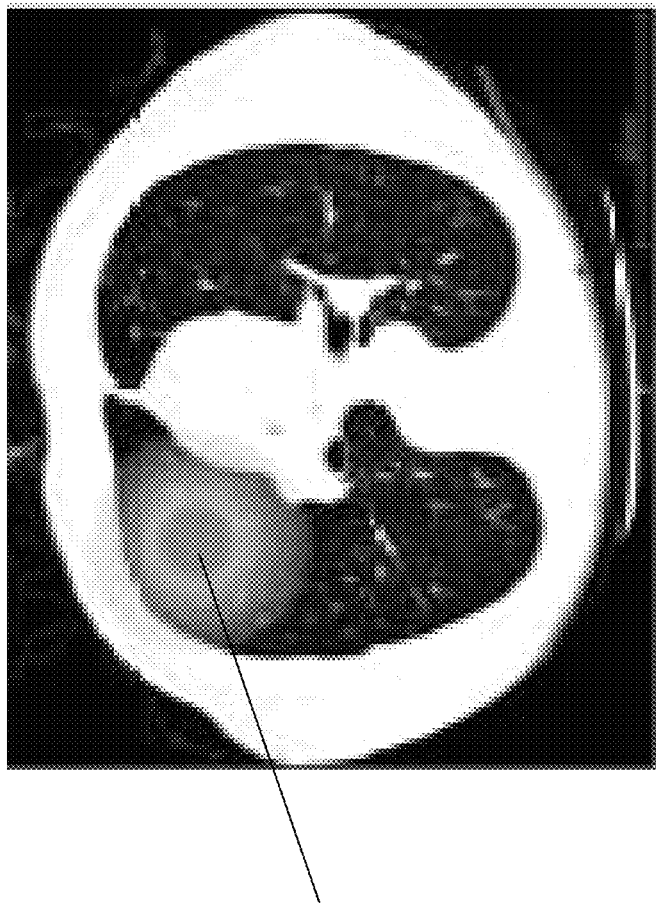
FIG. 5 depicts an example rendered image with highlighted pathological changes.

FIG. 5 depicts an example of a highlighted change in a follow up CT image. The pathological change may be identified by analyzing the aligned images. The analysis may provide a heat map or a location where a pathological change is detected between the aligned images. The rendered image may include a highlighted pathological change 80. The highlighted pathological change 80 may be highlighted using symbols or colors, for example.

Figure 6:
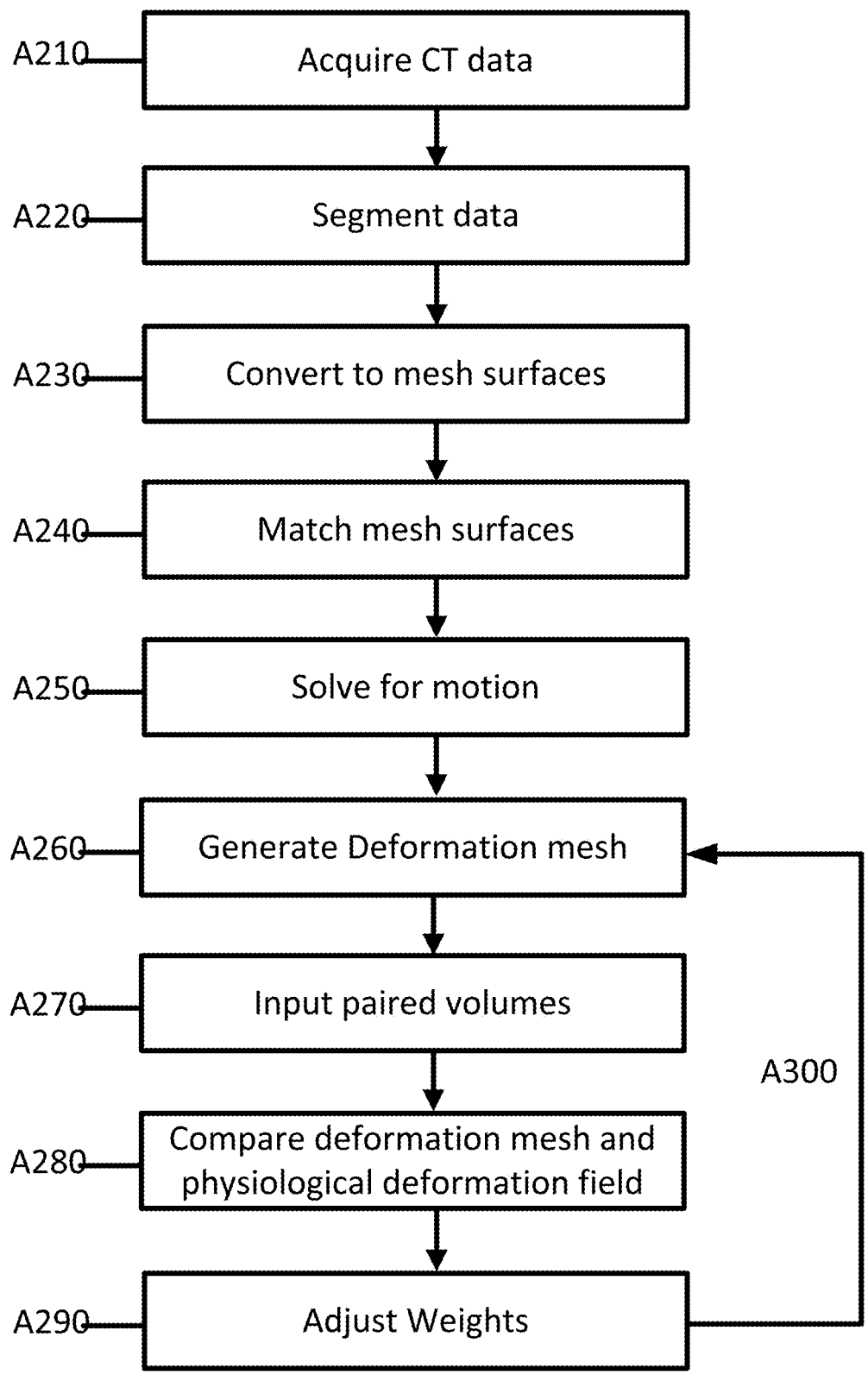
FIG. 6 depicts a method for training a machine-learned network to detect pathological changes in CT images acquired at two or more time points according to an embodiment.

FIG. 6 depicts one embodiment of a method for training a neural network to generate a physiological deformation field between a reference CT volume and a follow up CT volume. The acts are performed by the system of FIG. 1, FIG. 4, FIG. 7, other systems, a workstation, a computer, and/or a server. The acts are performed in the order shown (e.g., top to bottom) or other orders.

At act A210, a plurality of paired reference CT volumes and follow up CT volumes are acquired. The CT volumes may be acquired for different patients over different time periods. The CT volumes may be acquired by different imaging devices. A biomechanical model is generated from the plurality of paired reference CT volumes and follow up CT volumes. For lung scans, the biomechanical model may include structures such as lung surfaces, the lobes, the airways, blood vessel, anatomical landmarks, etc. The biomechanical model is generated by segmenting the CT volumes, generating meshes, and solving for motion. Once generated, the biomechanical model may be updated with newly acquired CT volumes. Different biomechanical models may be used for different types of patients. For example, depending on weight, body size, gender, or age etc. an organ (e.g. lung) may operate differently.

At act A220, the plurality of pairs of CT volumes are segmented. The lungs and relevant constitutive anatomy are segmented from the CT data (acquired at multiple time points and phases in order to capture the biomechanical motion of the lung anatomy). Any method for segmentation may be used. For example, segmentation may be thresholding-based, region-based, shape-based, model based, neighboring based, and/or machine learning-based among other segmentation techniques. Thresholding-based methods segment the image data by creating binary partitions based on image attenuation values, as determined by the relative attenuation of structures on the CT images. Region-based segmentation compares one pixel in a CT image to neighboring pixels, and if a predefined region criterion (e.g. homogeneity) is met, then the pixel is assigned to the same class as one or more of its neighbors. Shape-based techniques use either an atlas-based approach or a model-based approach to find a lung boundary. Model-based methods use prior shape information, similar to atlas-based approaches; however, to better accommodate the shape variabilities, the model-based approaches fit either statistical shape or appearance models of the lungs to the image by using an optimization procedure. Neighboring anatomy-guided methods use the spatial context of neighboring anatomic objects of the lung (e.g. rib cage, heart, spine) for delineating lung regions. In machine learning-based methods, the lung abnormalities and boundaries are predicted on the basis of the features extracted from the image data.

At act A230, the segmented pairs are converted to a plurality of mesh surfaces that describe the structures of the lungs.

At act A240, the mesh surfaces of the plurality of pairs of CT volumes are matched using point-wise correspondences. The meshes are matched in paired volumes//images from the reference and follow-up CT data by generating point-wise correspondences (e.g. all the points on the lung surfaces are matched, all the points on the blood vessels are matched, etc.). The matching may be accomplished by using an algorithm such as coherent point drift (CPD) or other point- or surface-based registration method such as iterative closest point (ICP). CPD is a method for non-rigid registration of two-point sets. Registration is a maximum likelihood estimation problem, where one-point set represents centroids of a gaussian mixture module and the other represents the data. CPD uses motion and velocity of points for registration.

At act A250, motion for the matched mesh surfaces is solved using a finite element method or other discrete solver method. Once the point-wise correspondences are generated for the lung segmentations, the correspondences are used as boundary conditions to an appropriate biomechanical model describing the tissue motion of interest. A finite element method (FEM) solution is used for the equations of motion describing the modes of lung deformation. The organ domain is discretized as a tetrahedral mesh from the geometry of the lung segmentation surface. A 3D Navier-Cauchy equation is used for the tissue displacement field at static equilibrium:

$$\frac{E}{2(1+v)(1-2v)}\nabla(\nabla \cdot u) + \frac{E}{2(1+v)}\nabla^2 u + F = 0$$

where E is Young's modulus, v is Poisson's ratio, u is the 3D displacement vector at a point in the tissue, and F is the applied body force distribution. The displacements at each point of the tissue are solved for such that the equation is satisfied.

Linear basis functions are defined on the tetrahedral elements and perform the Galerkin weighted residual method to construct a linear system of equations with the form:

$$Ku=f$$

where K is the stiffness matrix containing contributions from the material properties and constitutive equation, u is the vector of mesh nodal displacements, and f contains a vector of applied boundary conditions. Patient-specific boundary conditions are generated for f by using CPD to determine correspondence vectors between the two sets of lung segmentation meshes.

Alternative methods may be used to generate or augment the biomechanical model. For example, a stress distribution model and a numerical implementation based on the finite element method (FEM) may be used for the lungs. The FEM provides a framework that allows for the relationships between stress, strain, and force loads on a target to be expressed in terms of a motion field that more realistically describes the underlying physiology. FEM may be used to solve for the complex elasticity problem of lungs. Lung motion may also be modelled as a contact problem to be solved by the FEM. Ventilation, for example, may be modeled using the lung geometry. At exhale, the lung geometry is inflated by applying a negative pressure in accordance with elasticity theory until it matches a final lung shape at inhale.

At act A260, a deformation mesh is generated for a paired set of CT volumes using the mesh surfaces and the motion. The biomechanical model outputs a mesh deformation that may be converted (rasterized) into an image grid as a deformation field. The deformation describes the anatomical movement of the lung tissues. Different images taken at different times may be compared. For example, inspiratory (INSP) and expiratory (EXP) images may be compared to identify the deformation of the lung. The deformation may also describe the magnitude of the movement. For example, the deformation of a first portion of the lungs may be greater than another portion. The deformation field may describe the difference using a larger value for the first portion than the other portion. As a patient inhales or exhales the shape of the lung changes. The lower portions of the lungs may exhibit large deformations than, for example, the center of the lung.

At act A270, the paired set of CT volumes is input into the neural network configured to output a physiological deformation field. An image-to-image neural network is trained to generate a generated deformation field when input a first CT reference volume of the reference CT volume data and a first CT follow up volume of the follow up CT volume data. The image-to-image neural network is trained using a difference between the deformation field and the generated deformation field as a loss function. For training, the image-to-image neural network takes two CT images (image data, image volumes) into its input layer, and the output layer is a generated deformation field image that is compared to a model-generated field.

At act A280, the deformation mesh is compared and the physiological deformation field. The deformation comparison is used as a loss function to train the image-to-image neural network.

At act A290, weights are adjusted in the machine network as a function of the comparison. The loss is used to iteratively adjust the internal weights of the image-to-image neural network until the network is able to generate deformation fields that are similar to the modelled deformations across the large cohort of training data.

At act A300, generating (A260), inputting (A270), comparing (A280), and adjusting (A290) are repeated with paired sets of CT volumes until the neural network outputs a physiological deformation field that is similar to the deformation field. The generated deformation field is used to align any new pairs of CT follow up images.

The biomechanical model and the trained machine network may be stored for later use. Additional follow-up procedures may be performed for additional patients. The biomechanical model and the trained machine network may be used or augmented during the additional procedures.

FIG. 7 depicts an embodiment of a system for identifying pathological changes in follow up CT data. The system includes a control unit 20, an imaging system 100 (here depicted as a CT imaging system 100), and a server 28. The control unit 20 includes an image processor 22, a memory 24, a display 26, and a machine-learned network 30. Additional, different, or fewer components may be provided. For example, network connections or interfaces may be provided, such as for networking with a medical imaging network or data archival system. In another example, a user interface is provided as part of the display 26 or imaging system 100. In yet other embodiments, the server 28 or CT imaging system 100 are not provided.

The image processor 22, memory 24, and display 26, machine-learned network 30 are part of the control unit 20. Alternatively, the image processor 22, memory 24, and machine-learned network 30 are part of an archival and/or image processing system, such as associated with a medical records database workstation or server, separate from the imaging system 100. In other embodiments, the image processor 22, machine-learned network 30, and memory 24 are a personal computer, such as desktop or laptop, a workstation, a server 28, a network, or combinations thereof. The image processor 22, display 26, machine-learned network 30, and memory 24 may be provided without other components for acquiring data by scanning a patient.

The control unit 20, image processor 22, memory 24, display 26, machine-learned network 30, and imaging system 100 are provided at a same location. The location may be a same room, same building, or same facility. The devices are local relative to each other and are remote to the server 28. The server 28 is spaced apart by a network by being in a different facility or by being in a different city, county, state, or country. The server 28 may be remote from the location of the imaging system 100.

The imaging system 100 is a medical diagnostic imaging system. Computed tomography (CT), X-ray, ultrasound, and/or magnetic resonance (MR) systems may be used. The imaging system 100 may include a transmitter and includes a detector for scanning or receiving data representative of the interior of the patient. The imaging system 100 is configured to acquire image slices (2D) or an image volume (3D). The imaging system 100 may acquire a plurality of image volumes over time that may be used to generate a video.

In one embodiment, the imaging system 100 is a CT or X-ray system. An X-ray source connects to a gantry. A detector is also connected with the gantry opposite the X-ray source. The patient is positioned between the source and detector. The source and detector are on opposite sides of the patient and rotate and/or translate about the patient. The detected X-ray energy passing through the patient is converted, reconstructed, or transformed into data representing different spatial locations within the patient. In an embodiment, the imaging system 100 may include a portable or mobile C-arm. The C-arm includes an X-ray source and an image intensifier or flat-panel detector. The C-shaped connecting element allows movement horizontally, vertically and around the swivel axes, so that X-ray images of the patient may be produced from almost any angle. The generator emits X-rays that penetrate the patient's body. The image intensifier or detector converts the X-rays into a visible image displayed on a monitor or stored for later use.

In another embodiment, the imaging system 100 is an MR system. The MR system includes a main field magnet, such as a cryo-magnet, and gradient coils. A whole-body coil is provided for transmitting and/or receiving. Local coils may be used, such as for receiving electromagnetic energy emitted by atoms in response to pulses. Other processing components may be provided, such as for planning and generating transmit pulses for the coils and for receiving and processing the received k-space data. The received k-space data is converted into object or image space data with Fourier processing.

The memory 24 may be a graphics processing memory, a video random access memory, a random-access memory, system memory, cache memory, hard drive, optical media, magnetic media, flash drive, buffer, database, combinations thereof, or other now known or later developed memory device for storing data or video information. The memory 24 is part of the imaging system 100, part of a computer associated with the image processor 22, part of a database, part of another system, a picture archival memory, or a standalone device.

The memory 24 stores medical imaging data, graphical or display setting, and/or images. The memory 24 may store data during processing for application and/or may store training data for the machine-learnt network 30. The memory 24 may store data relating to a biomechanical model generated from data acquired from the CT imaging system 100.

The memory 24 or other memory is alternatively or additionally a non-transitory computer readable storage medium storing data representing instructions executable by the programmed image processor 22 for identifying pathological changes in follow up CT data (images or volumes). The instructions for implementing the processes, methods and/or techniques discussed herein are provided on non-transitory computer-readable storage media or memories, such as a cache, buffer, RAM, removable media, hard drive, or other computer readable storage media. Non-transitory computer readable storage media include various types of volatile and nonvolatile storage media. The functions, acts or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code, and the like, operating alone, or in combination. Likewise, processing strategies may include multiprocessing, multitasking, parallel processing, and the like.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

The machine-learned network 30 may be configured in software or hardware. The machine-learned network 30 may be part of the image processor and/or may be stored in the memory 24. The machine-learned network 30 may be trained on data stored in the memory 24 and/or acquired by the imaging system 100. The machine-learned network 30 may be configured to generate a physiological deformation field between a reference fixed CT volume and a follow up CT volume acquired by the CT imaging system 100 or stored in memory 24. The machine-learned network 30 may be configured to implement the biomechanical model in that the machine-learned network 30 may be configured to input a reference CT volume and a follow up CT volume and generate a deformation field similar to a deformation field generated by the biomechanical model. The machine-learned network 30 and/or the image processor 22 may be configured to align the reference CT volume and the follow up CT volume based on the deformation field. The machine-learned network 30 may input and process either two dimensional or three dimensional data (images or volumes).

The image processor 22 is a general processor, central processing unit, control processor, graphics processing unit, digital signal processor, three-dimensional rendering processor, image processor, application specific integrated circuit, field programmable gate array, digital circuit, analog circuit, combinations thereof, or other now known or later developed device for rendering a two-dimensional image from an image volume. The image processor 22 is a single device or multiple devices operating in serial, parallel, or separately. The image processor 22 may be a main processor of a computer, such as a laptop or desktop computer, or may be a processor for handling some tasks in a larger system, such as in the imaging system 100 or the server 28. The image processor 22 is configured by instructions, design, hardware, and/or software to perform the acts discussed herein.

The image processor 22 and/or server 28 are configured to perform the acts discussed above for identifying pathological changes in follow up CT data. The image processor 22 is configured to warp the follow up moving CT volume as a function of the physiological deformation field. The image processor 22 is further configured to subtract the warped follow up moving CT volume from the reference fixed CT volume. The image processor 22 is further configured to highlight the differences between the warped follow up moving CT volume and the reference fixed CT volume as the pathological changes.

The image processor 22 and/or server 28 are configured to provide an image to the display 26 or to the memory 24. The display 26 is a monitor, LCD, projector, plasma display, CRT, printer, or other now known or later developed devise for outputting visual information. The display 26 receives images, graphics, text, quantities, or other information from the image processor 22, memory 24, imaging system 100, and/or server 28. The display 26 is configured to provide image volumes to an operator.

The control unit 20 may also include a user interface (not shown) that is configured to receive one or more selections from a user. The user interface may include an input device such as one or more buttons, a keypad, a keyboard, a mouse, a stylus pen, a trackball, a rocker switch, a touch pad, a voice recognition circuit, or other device or component for inputting data. The user interface and the display 26 may be combined as a touch screen that may be capacitive or resistive.

The server 28 connects to the imaging system 100 via a network. The network is a local area, wide area, enterprise, another network, or combinations thereof. In one embodiment, the network is, at least in part, the Internet. Using TCP/IP communications, the network provides for communication between the image processor 22 and the server 28. Any format for communications may be used. In other embodiments, dedicated or direct communication is used.

The server 28 is a processor or group of processors. More than one server 28 may be provided. The server 28 is configured by hardware and/or software. The server 28 may include one or more image processors 22. The one or more image processors 22 may operate serially or in parallel to process and render image data received from the CT imaging system 100. The server 28 may generate and store a biomechanical model based on CT data acquired from the CT imaging system 100 or stored in memory 24.

In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU, or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A method for identifying pathological changes in follow up medical images, the method comprising:
   acquiring, by an imaging system, reference image data at a first time;
   acquiring, by the imaging system, follow up image data at a subsequent time;
   generating, by a processor, a deformation field for the reference image data and the follow up image data using a machine-learned network trained to generate deformation fields describing healthy, anatomical deformation between input reference image data and input follow up image data;
   aligning, by the processor, the reference image data and the follow up image data using the deformation field; and
   analyzing, by the processor the co-aligned reference image data and follow up image data for changes due to pathological phenomena.

2. The method of claim 1, wherein the machine-learned network is trained using a loss function derived from a deformation field generated by a biomechanical model of soft tissue deformation.

3. The method of claim 2, wherein the biomechanical model is generated from a plurality of reference image data and follow up image data.

4. The method of claim 3, wherein the biomechanical model is generated by:
   segmenting, by the processor, pairs of the plurality of reference image data and the plurality of follow up image data;
   converting, by the processor, the segmentation to mesh surfaces;
   matching, by the processor, the mesh surfaces between pairs the plurality of reference image data and the follow up image data by generating point-wise correspondences between the reference image data and follow up image data; and
   solving, by the processor, for motion for the matched mesh surfaces using a biomechanical model of organ deformations, solved using a discrete solver method.

5. The method of claim 1, wherein the machine-learned network is a deep three-dimensional convolutional image-to-image neural network.

6. The method of claim 1, further comprising:
   rendering, by the processor, an image of the aligned follow up image data; and
   displaying, by the processor, the image with the changes due to pathological phenomena highlighted.

7. The method of claim 1, wherein analyzing comprises:
   analyzing, by the processor, using a neural network trained to recognize patch-wise changes in the co-aligned reference image data and follow up image data.

8. The method of claim 1, wherein reference image data and follow up data is computed tomography image data.

9. The method of claim 1, wherein the reference image data and the follow up image are acquired by different imaging systems.

10. The method of claim 1, wherein the second time is at least after enough time to observe anatomical changes due to the disease or a therapy.

11. A method for training a neural network to generate a physiological deformation field between a reference volume and a follow up volume, the method comprising:
   acquiring a plurality of paired reference volumes and follow up volumes;
   segmenting the plurality of pairs of volumes;
   converting the segmented pairs to a plurality of mesh surfaces;
   matching the mesh surfaces of the plurality of pairs of volumes using point-wise correspondences;
   solving for motion for the matched mesh surfaces using a biomechanical model of organ deformations, solved using a discrete solver method;
   generating a deformation mesh for a paired set of volumes using the mesh surfaces and the motion;
   inputting the paired set of volumes into the neural network configured to output a physiological deformation field;
   comparing the deformation mesh and the physiological deformation field;
   adjusting weights in the neural network as a function of the comparison; and
   repeating generating, inputting, comparing, and adjusting with paired sets of volumes until the neural network outputs a physiological deformation field that is similar to the deformation field.

12. The method of claim 11, wherein the plurality of paired reference volumes and follow up volumes are acquired with different time intervals.

13. The method of claim 11, wherein the plurality of paired reference volumes and follow up volumes comprise lung volumes.

14. The method of claim 11, wherein the reference volume and follow up volume are acquired by a computed tomography imaging system.

15. A system for identifying pathological changes in follow up medical images for a patient, the system comprising:
   a machine-learned network configured to generate a physiological deformation field between a reference image and a follow up image; and an image processor configured to warp the follow up image as a function of the physiological deformation field; the image processor further configured to identify a difference from the warped follow up image from the reference image; the image processor further configured to highlight the difference between the warped follow up image and the reference image as the pathological changes.

16. The system of claim 15, wherein the machine-learned network is trained to regress a ground truth of physiological deformation generated from a biomechanical model of the patient.

17. The system of claim 16, wherein the biomechanical model is configured to model deformation of a lung volume of the patient.

18. The system of claim 17, wherein the biomechanical model is derived from a plurality of reference images and a plurality of follow up images of the patient.

19. The system of claim 15, further comprising:
a display configured to display, as an image, the highlighted differences on the warped follow up moving image.

20. The system of claim 19, wherein the image is a heatmap.

* * * * *